United States Patent
Aoki et al.

(10) Patent No.: US 7,397,016 B2
(45) Date of Patent: Jul. 8, 2008

(54) HEAT GENERATING ELEMENT, MEDICAL THERAPEUTIC INSTRUMENT IMPLEMENTING THE SAME, AND TREATMENT APPARATUS

(75) Inventors: Yukihiro Aoki, Okaya (JP); Toru Nagase, Tachikawa (JP)

(73) Assignees: Olympus Corporation, Tokyo (JP); Olympus Medical Systems Corp., Tokyo (JP)

(*) Notice: Subject to any disclaimer, the term of this patent is extended or adjusted under 35 U.S.C. 154(b) by 251 days.

(21) Appl. No.: 11/142,739

(22) Filed: Jun. 1, 2005

(65) Prior Publication Data

US 2005/0288747 A1    Dec. 29, 2005

(30) Foreign Application Priority Data

Jun. 8, 2004    (JP)    ............................. 2004-170336

(51) Int. Cl.
*A61B 18/08* (2006.01)
*H05B 3/12* (2006.01)
*H05B 3/16* (2006.01)

(52) U.S. Cl. ...................... 219/229; 219/225; 219/543; 219/548; 219/553; 606/28; 607/96; 607/112

(58) Field of Classification Search ................. 219/221, 219/225, 227, 229, 536, 542, 543, 552, 553; 606/46, 48, 51

See application file for complete search history.

(56) References Cited

U.S. PATENT DOCUMENTS

| 728,883 | A | | 5/1903 | Downes |
| 5,504,307 | A | * | 4/1996 | Hayashi et al. ............. 219/543 |
| 5,665,262 | A | * | 9/1997 | Hajaligol et al. ............ 219/553 |
| 2003/0171747 | A1 | | 9/2003 | Kanehira et al. |
| 2003/0208201 | A1 | * | 11/2003 | Iida et al. ....................... 606/51 |

FOREIGN PATENT DOCUMENTS

| EP | 1 341 215 A1 | 9/2003 |
| JP | 9-232102 | 9/1997 |
| JP | 2003-70801 | 3/2003 |
| JP | 3523839 | 2/2004 |
| WO | WO 02/41370 A2 | 5/2002 |

* cited by examiner

*Primary Examiner*—Joseph M Pelham
(74) *Attorney, Agent, or Firm*—Scully, Scott, Murphy & Presser, P.C.

(57) ABSTRACT

A heat generating element is constructed of at least a substrate, an insulating film disposed on the substrate, a heat generating portion provided with a thin film resistor disposed on at least a part of the insulating film, and a protective film disposed on the above-described insulating film and the above-described heat generating portion, wherein the above-described substrate and the above-described heat generating portion are composed of the same member. Additionally, a medical therapeutic instrument includes a treatment portion provided with the above-described heat generating element to heat a living body tissue by using the heat generated from the heat generating element and treat the living-body tissue. The heat generating element is mounted on the above-described treatment portion in such a manner that an outer surface of the above-described substrate of the heat generating element serves as a treatment surface.

29 Claims, 14 Drawing Sheets

FIG.13
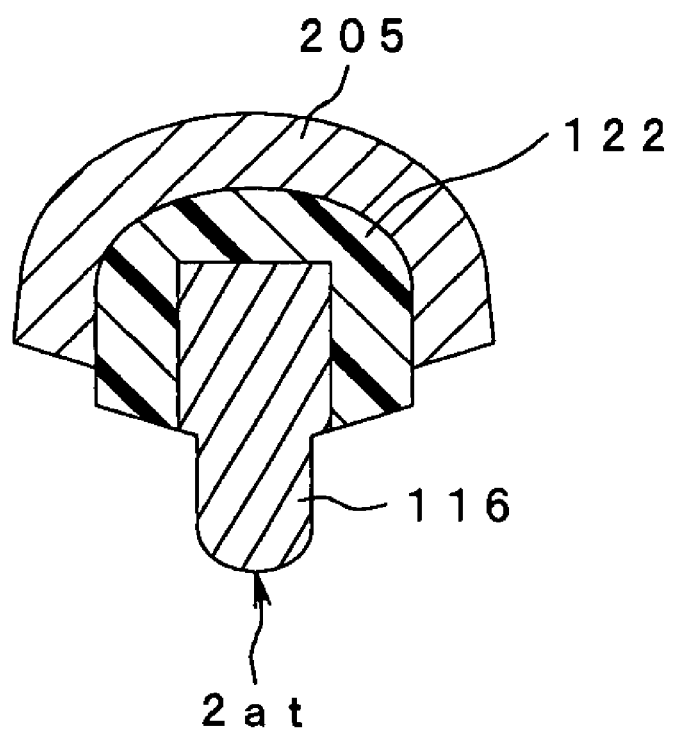
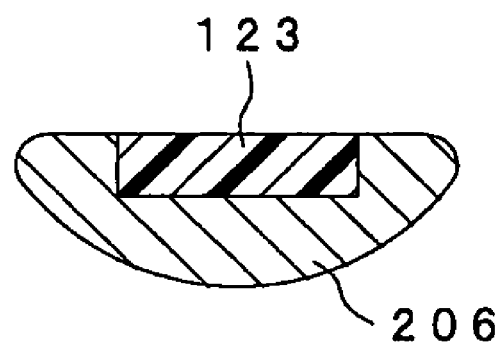

HEAT GENERATING ELEMENT, MEDICAL THERAPEUTIC INSTRUMENT IMPLEMENTING THE SAME, AND TREATMENT APPARATUS

This application claims benefit of Japanese Application No. 2004-170336 filed in Japan on Jun. 8, 2004, the contents of which are incorporated by this reference.

BACKGROUND OF THE INVENTION

1. Field of the Invention

The present invention relates to a heat generating element which generates heat in the treatment of a living body tissue by heating, a medical therapeutic instrument implementing the heat generating element, and a treatment apparatus.

2. Description of the Related Art

Various medical accessories have been previously proposed. The medical accessories are inserted into body cavities to heat living-body tissues and, for example, coagulate the living-body tissues.

For example, Japanese Patent No. 3523839 discloses a surgical instrument serving as a medical therapeutic instrument having a pair of jaws which are opened and closed through a pivotal portion disposed at the proximal end portions.

In the surgical instrument disclosed in Japanese Patent No. 3523839, a heat generating plate is disposed on the distal-end side in the inside of one jaw of a pair of jaws in the surgical instrument, and the heat generating plate is in the shape of a taper having a width decreasing with increasing proximity to a lower end edge.

A portion of the heat generating plate exposed at the one of the jaws constitutes a treatment surface in the treatment of a living-body tissue by heating, coagulating, cutting, and the like. Furthermore, thin film resistance heating elements are disposed on the perimeter surface of the exposed portion of the heat generating plate, that is, on the treatment surface. The thin film resistance heating elements are electrically connected to a lead wire on the proximal-end side of the one of the jaws. The thin film resistance heating elements are formed by superimposing an insulating layer, a resistor serving as a heat generating portion, a protective layer, and a Teflon coating layer on the heat generating plate in that order to constitute a four-layer structure.

The thus configured surgical instrument disclosed in Japanese Patent No. 3523839 is used for heating a living-body tissue by taking advantage of heat generation of the resistor of the thin film resistance heating elements disposed on the heat generating plate based on the electric power supplied from a power device, so as to, for example, coagulate the living-body tissue.

Japanese Unexamined Patent Application Publication No. 2003-70801 discloses a surgical instrument including a pair of jaws which are optionally opened and closed and which serve as a medical therapeutic instrument used for heating a living-body tissue to, for example, coagulate the living-body tissue.

In the surgical instrument disclosed in Japanese Unexamined Patent Application Publication No. 2003-70801, a heat generating element is mounted on the side-surface side in the inside of one of the jaws in the surgical instrument, and heat generating patterns, e.g., thin film resistance heating elements divided into two parts, for example, a front portion and a rear portion, are disposed on the side surface in the vicinity of an edge portion of the heat generating element.

The thus configured surgical instrument disclosed in Japanese Unexamined Patent Application Publication No. 2003-70801 is used for heating a living-body tissue by taking advantage of heat generation of the heat generating patterns disposed on the heat generating element based on the electric power supplied from a power device, so as to coagulate the living-body tissue.

In addition, a heating member disclosed in Japanese Unexamined Patent Application Publication No. 9-232102 is formed by disposing a resistance layer on a metal substrate, and can be used not only for a medical therapeutic instrument, but also for various purposes.

The heating member is composed of a substrate made of anodized aluminum, aluminum, stainless steel, enamel-coated steel, copper, or the like, an electrically insulating layer disposed on the substrate and made of a silicone resin containing a thermally conductive filler, an electrical resistance layer disposed on the electrically insulating layer and made of a silicone resin containing an electrically conductive filler, an electrically conductive region disposed on a part of the electrical resistance layer, and an insulating protective coating layer disposed on the electrical resistance layer.

The thus configured heating member disclosed in Japanese Unexamined Patent Application Publication No. 9-232102 can improve the resistance against high temperatures and high power densities.

SUMMARY OF THE INVENTION

A heat generating element according to an aspect of the present invention includes at least a substrate, an insulating film disposed on the substrate, a heat generating portion having a thin film resistor disposed on at least a part of the insulating film, and a protective film disposed on the above-described insulating film and the above-described heat generating portion, wherein the above-described substrate and the above-described heat generating portion are composed of the same member.

A medical therapeutic instrument implementing a heat generating element according to another aspect of the present invention includes the above-described heat generating element and a treatment portion provided with the heat generating element to heat a living body tissue by using the heat generated from the heat generating element and treat the living-body tissue, wherein the above-described heat generating element is mounted on the above-described treatment portion in such a manner that an outer surface of the above-described substrate of the heat generating element serves as a treatment surface in the treatment of the living-body tissue.

Furthermore, a treatment apparatus according to another aspect of the present invention includes the above-described medical therapeutic instrument and means to supply electric power to the above-described heat generating element disposed on the above-described medical therapeutic instrument.

The above and other objects, features and advantages of the invention will become more clearly understood from the following description referring to the accompanying drawings.

BRIEF DESCRIPTION OF THE DRAWINGS

FIG. 13 is a sectional view of the section taken along a line XIII-XIII shown in FIG. 12.

DETAILED DESCRIPTION OF THE PREFERRED EMBODIMENTS

The embodiments of the present invention will be described below with reference to the drawings.

First Embodiment

Figure 1:
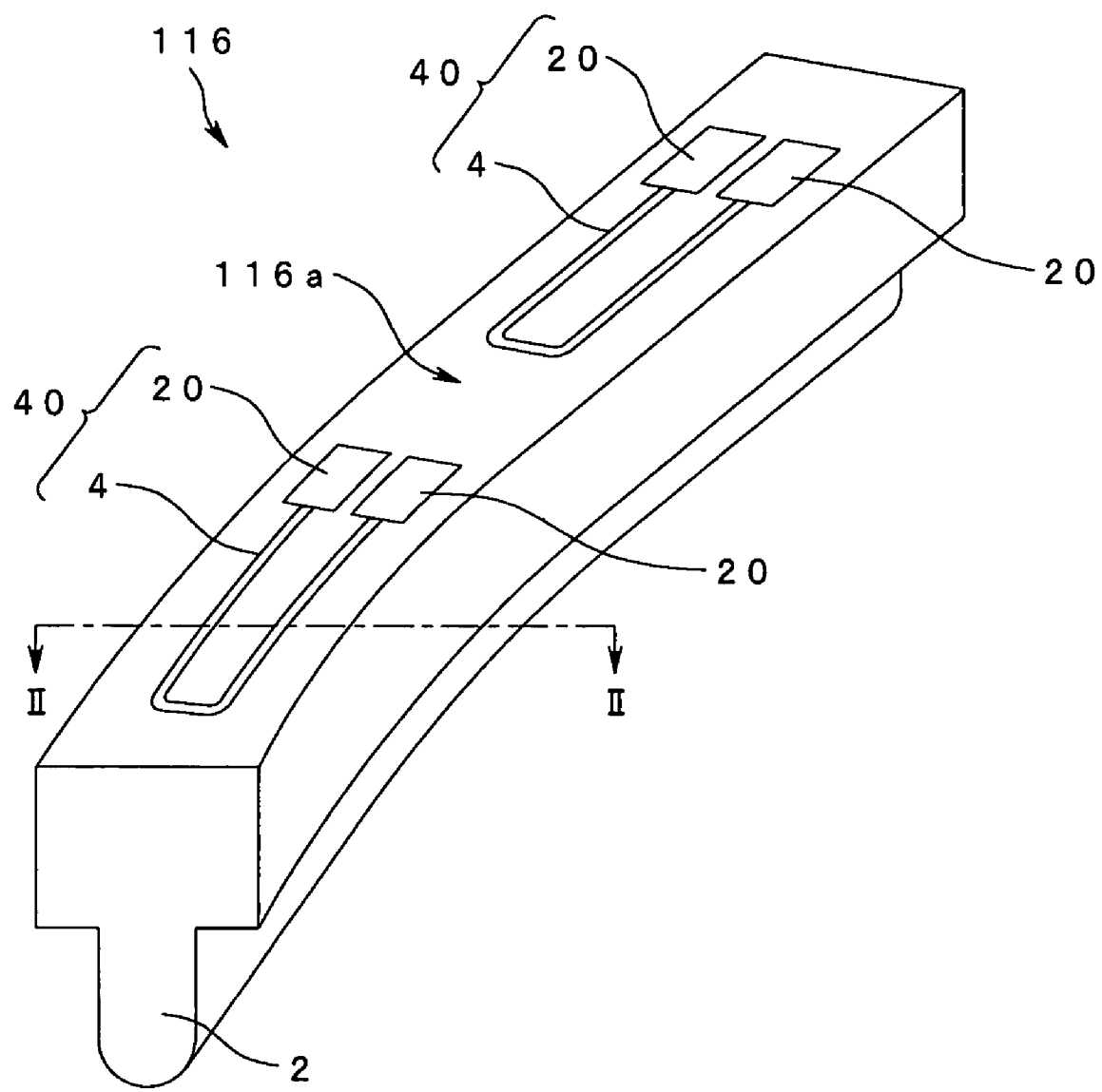
FIG. 1 is a perspective view of a heat generating element according to a first embodiment of the present invention.
Figure 2:
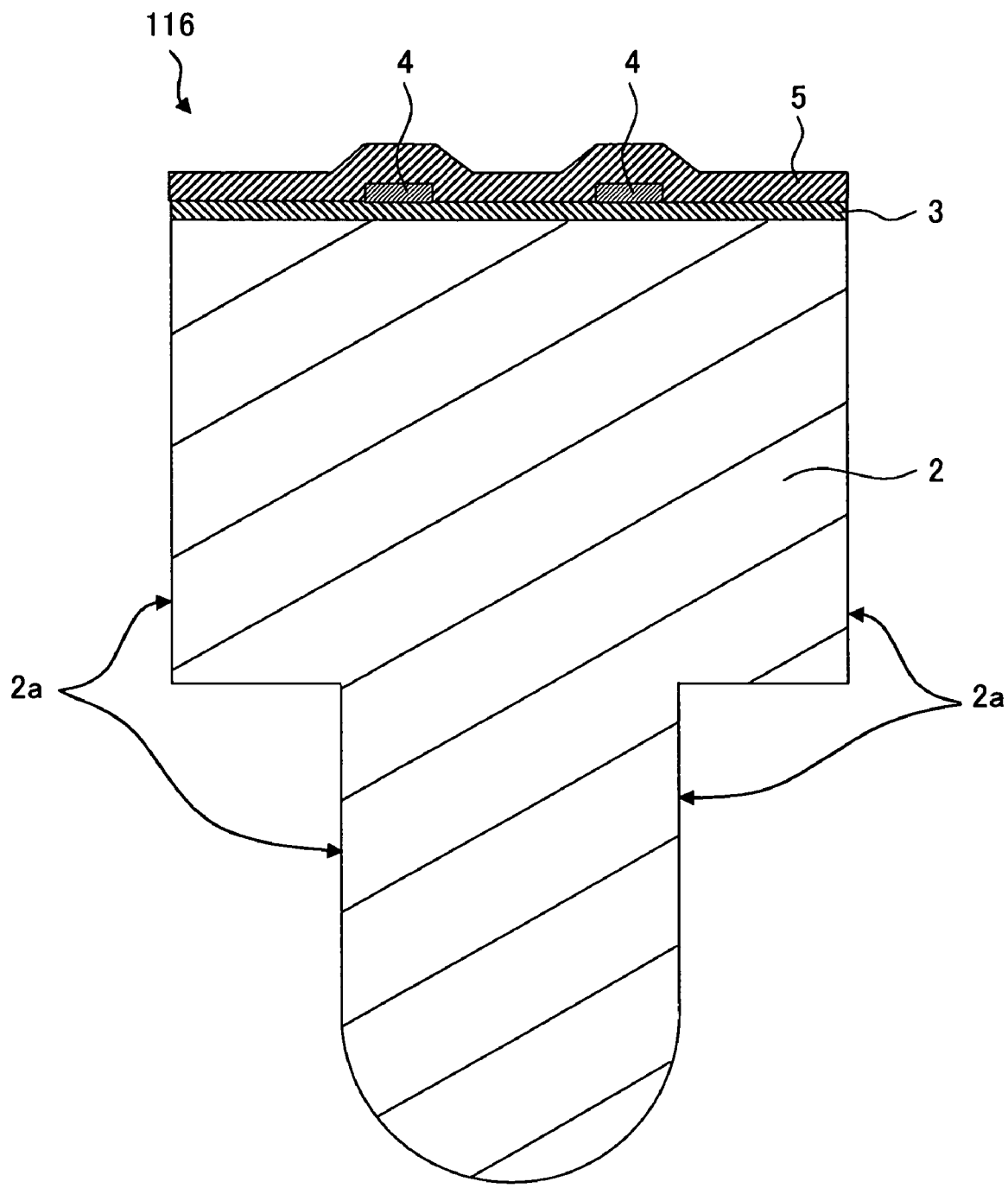
FIG. 2 is a sectional view of the section taken along a line II-II shown in FIG. 1.

FIG. 1 is a perspective view of a heat generating element according to the first embodiment of the present invention. FIG. 2 is a sectional view of the section taken along a line II-II shown in FIG. 1.

As shown in FIG. 1, a heat generating element 116 is formed into the shape of a free-form surface, for example, a curved shape, in a longitudinal direction (hereafter referred to as principal axis direction).

For example, two heat generating zones 40, each composed of a heat generating portion 4 described below and, for example, two electrodes 20 connected to the heat generating portion 4, are disposed on the top surface 116a of the heat generating element 116 along the principal axis of the heat generating element 116.

The electrode 20 is composed of a member suitable for wiring, e.g., copper, and transfers the electric power supplied from a power device, although not shown in the drawing, to the heat generating portion 4. The number of heat generating zones to be disposed are not limited to two, and may be one, or two or more in accordance with the length of the principal axis of the heat generating element 116.

As shown in FIG. 2, an insulating film 3 composed of, for example, a silicon nitride film is disposed on a substrate 2 composed of, for example, a high-melting point metal, molybdenum. The heat generating portion 4 made of a thin film resistor composed of the same member as that of the substrate 2 is disposed on the insulating film 3. A protective film 5 composed of, for example, a silicon nitride film is disposed on the heat generating portion 4 and the insulating film 3. The substrate 2, the insulating film 3, the heat generating portion 4, and the protective film 5 are disposed integrally.

The member of the substrate 2 is not limited to molybdenum. The substrate 2 may be composed of a member having a high heat conductivity. Examples thereof include high-melting point metals, alloys, and semiconductors, and specifically, noble metals, nickel-chromium, silicon, and tungsten.

A method for manufacturing the thus configured heat generating element 116 will be briefly described below.

The insulating film 3 composed of a silicon nitride film having a thickness of, for example, 50 to 2,000 nm is formed all over the substrate 2 composed of molybdenum through deposition by, for example, low pressure chemical vapor deposition (LP-CVD). The formation of the insulating film 3 is not limited to the deposition of the silicon nitride film, and may be performed by printing, application, and the like of other inorganic insulating films or organic insulating films.

Desirably, the insulating film 3 is made of a material having a coefficient of linear thermal expansion close to that of the substrate 2. Since the substrate 2 is composed of molybdenum having a coefficient of linear thermal expansion of $5.44 \times 10^{-6}$/K at room temperature, the insulating film 3 is composed of a silicon nitride film having the same order of coefficient of linear expansion, that is, $3.00 \times 10^{-6}$/K to $3.50 \times 10^{-6}$/K.

The heat generating portion 4 composed of a thin film resistor made of molybdenum, which is the same material as that of the molybdenum substrate 2, is formed on at least a part of the insulating film 3 in such a manner that the resulting film has a thickness capable of ensuring a heating value required for treating a living body, for example, a thickness of 50 to 2,000 nm, and takes on the shape of, for example, a letter U along the principal axis of the heat generating element 116, as shown in FIG. 1.

The formation of the heat generating portion 4 on the insulating film 3 is performed by, for example, a method in which molybdenum is deposited and patterned simultaneously by using a mask patterned into a desired shape of a letter U in evaporation or sputtering, or a method in which molybdenum is deposited all over the insulating film 3 and, thereafter, is photo-etched into the shape of a letter U.

The member of the insulating film 4 is not limited to molybdenum. The insulating film 4 may also be formed from a high-melting point metal, an alloy, or a semiconductor, e.g., a noble metal, nickel-chromium, silicon, or tungsten, as long as the member is the same as that of the substrate 2.

The protective film 5 composed of a silicon nitride film having a thickness of about 1.5 μm is formed on the heat generating portion 4 and the insulating film 3 through deposition by, for example, LP-CVD. As in the formation of the insulating film 3, the formation of the protective film 5 is not limited to the deposition of the silicon nitride film, and may be performed by printing, application, and the like of other inorganic insulating films or organic insulating films. Desirably, the protective film 5 is also made of a material having a coefficient of linear thermal expansion close to that of the substrate 2 and the heat generating portion 4, as in the insulating film 3.

Holes are formed in the protective film 5 on two proximal ends of each of two heat generating portions 4 in the shape of a letter U by using photo-etching. Four electrodes 20, that is, two electrodes 20 per heat generating zone 40, are formed from, for example, copper to have a thickness of, for example, 0.1 to 30 µm while covering the holes.

The formation of the electrodes 20 is performed by, for example, a method in which copper is deposited and patterned simultaneously by using a mask patterned into a desired shape in evaporation, sputtering, or plating, or a method in which copper is deposited all over the surface and, thereafter, is photo-etched into a desired shape.

Finally, the substrate 2 is formed into, for example, a substantially convex shape pointing downward through cutting by dicing, NC cutting, or the like. The heat generating element 116 is formed through the above-described steps.

In this manner, as for the heat generating element according to the first embodiment of the present invention, the substrate 2 and the heat generating portion 4 constituting the heat generating element 116 are composed of the same member. Therefore, there is almost no difference in coefficient of linear thermal expansion between the substrate 2 and the heat generating portion 4, so that the heat generating portion 4 is hardly influenced by strain due to the substrate 2 when heat is generated from the heat generating element 116. Consequently, no strain occur between the substrate 2 and the heat generating portion 4, the heat-generation resistance of the heat generating element 116 can be improved, and the heat generating element having a high heat-generation resistance can be provided.

In the present embodiment, the insulating film 3 and the protective film 5 are composed of the silicon nitride film having a coefficient of linear thermal expansion of $3.00 \times 10^{-6}$/K to $3.50 \times 10^{-6}$/K close to the coefficient of linear thermal expansion of the substrate 2 of $5.44 \times 10^{-6}$/K, so that an influence exerted on the heat generating portion 4 by strain due to the protective film 5 is reduced when heat is generated from the heat generating portion 4 of the heat generating element 116. Consequently, the heat-generation resistance of the heat generating element 116 can be improved, and the heat generating element 116 having a high heat-generation resistance can be provided.

In the present embodiment, the member of the substrate 2 is not limited to molybdenum. The substrate 2 may be composed of a member having a high heat conductivity. Examples thereof include high-melting point metals, alloys, and semiconductors, and specifically, noble metals, nickel-chromium, silicon, and tungsten. Since the heat generating zones 40, each provided with a heat generating portion 4, is disposed along the principal axis of the heat generating element 116, even when the heat generating element 116 is long-disposed in the principal axis direction, the uniformity of the temperature distribution of the heat generating element 116 can be improved in the heat generation.

In the present embodiment, as described above, the heat generating portion 4 constituting the heat generating zone 40 is formed into the shape of a letter U along the principal axis of the heat generating element 116. However, the shape is not limited to this, and the heat generating portion 4 may be formed into any shape, as a matter of course.

In the above description, two electrodes 20 are disposed on the proximal ends of each heat generating portions 4 in the shape of a letter U. However, the number of electrodes is not limited to this, and any number of electrodes may be disposed, as a matter of course.

Second Embodiment

Figure 3:
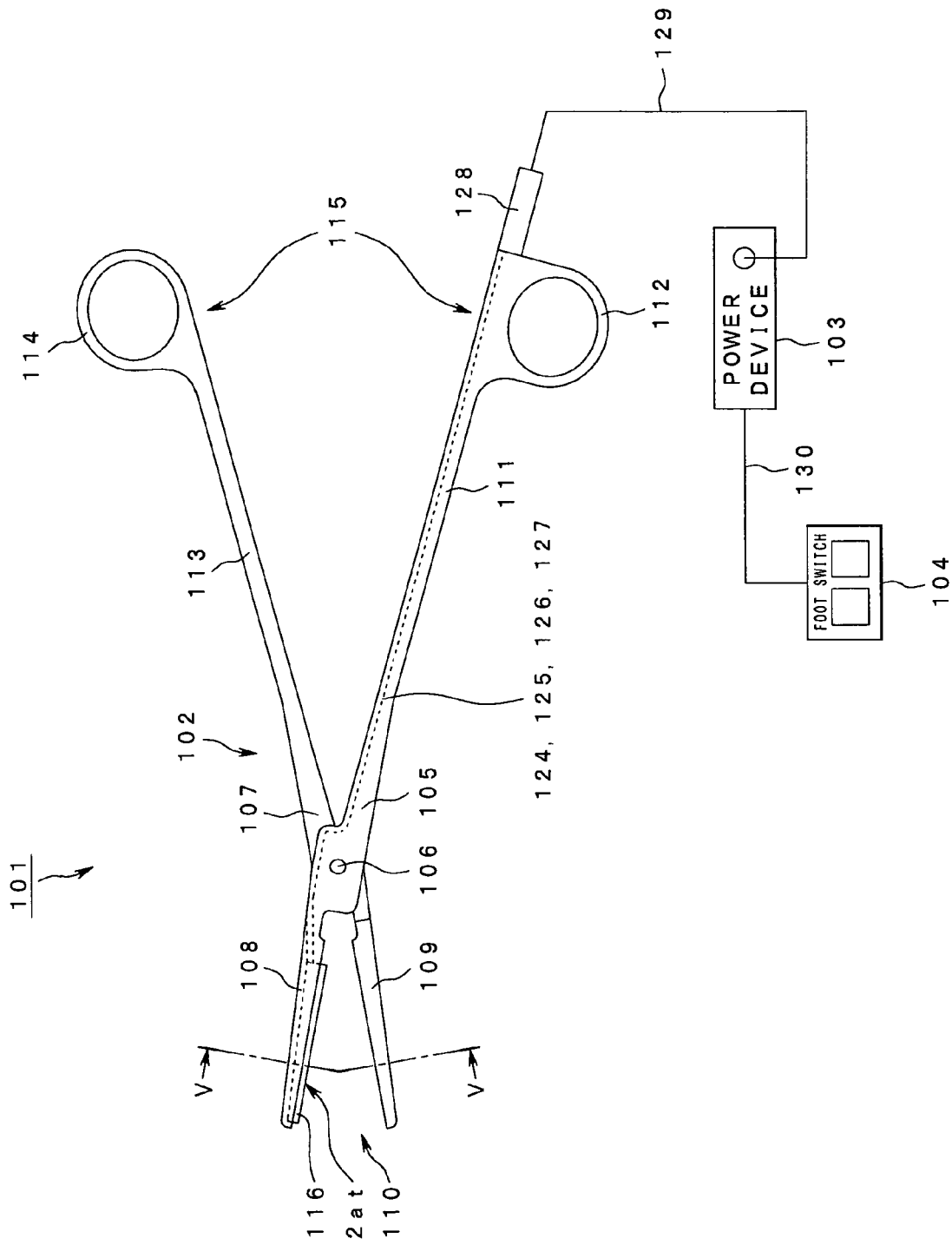
FIG. 3 is a front view showing a configuration of a treatment apparatus including a heat coagulation cutting forceps for open surgery, the forceps serving as a medical therapeutic instrument, and a power device according to a second embodiment of the present invention.
Figure 4:
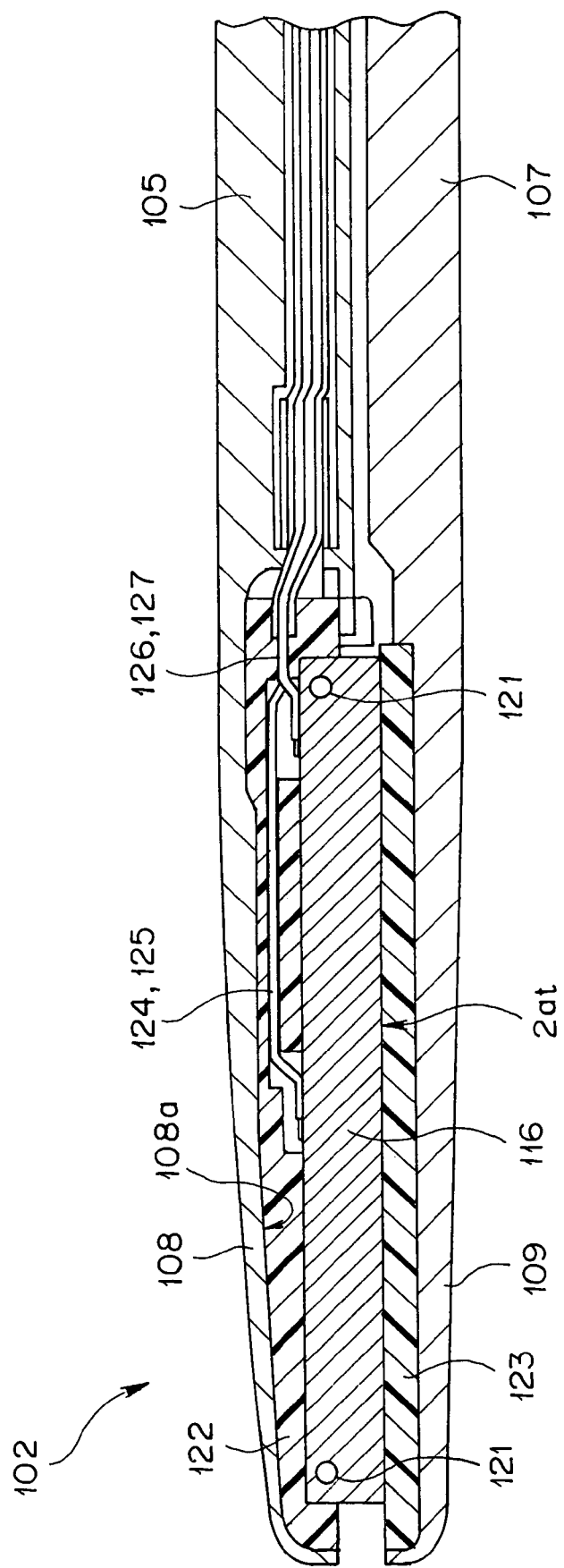
FIG. 4 is a sectional view of a distal end portion of the heat coagulation cutting forceps for open surgery shown in FIG. 3.
Figure 5:
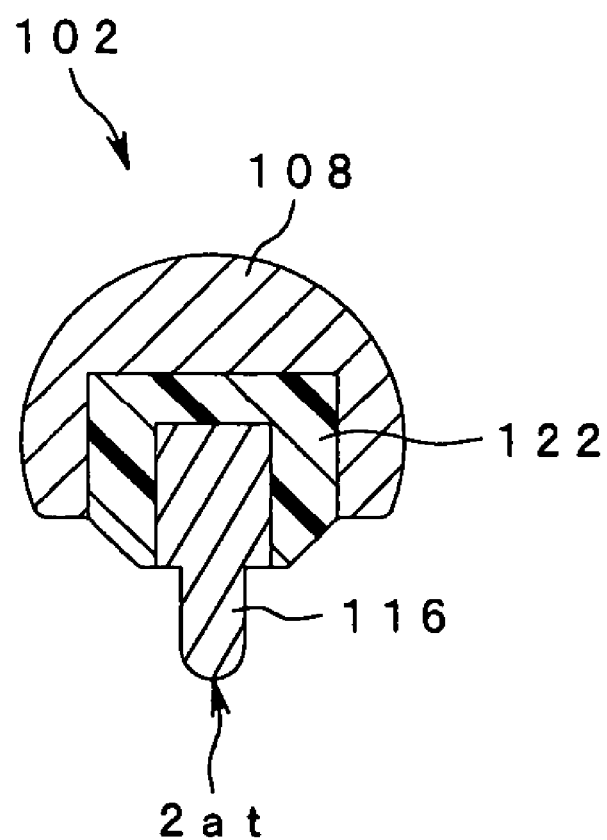
FIG. 5 is a sectional view of the section taken along a line V-V shown in FIG. 3.
Figure 6:
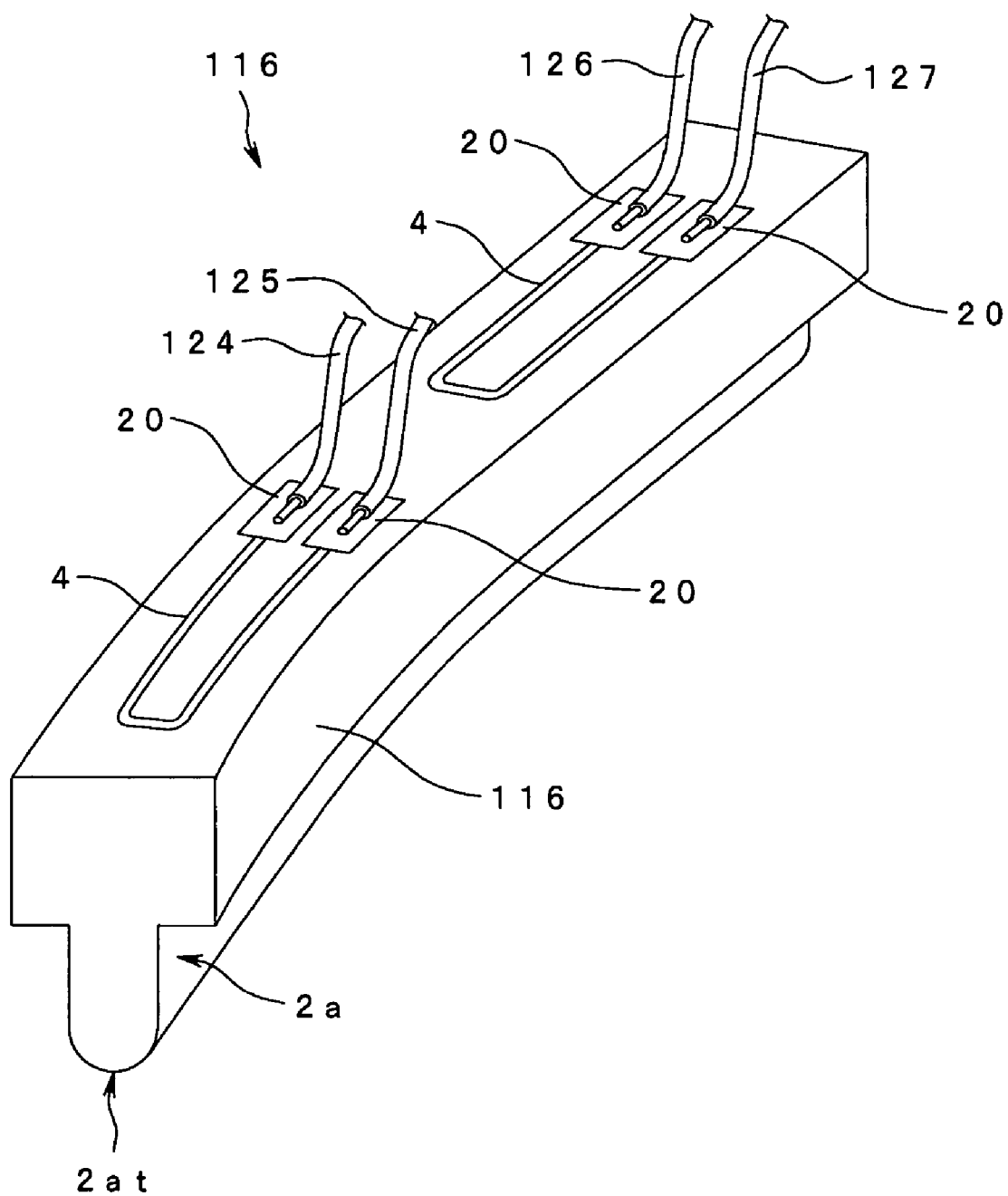
FIG. 6 is a magnified perspective view of the heat generating element shown in FIG. 3.

FIG. 3 is a front view showing a configuration of a treatment apparatus including a heat coagulation cutting forceps for open surgery, the forceps serving as a medical therapeutic instrument, and a power device according to the second embodiment of the present invention. FIG. 4 is a sectional view of a distal end portion of the heat coagulation cutting forceps for open surgery shown in FIG. 3. FIG. 5 is a sectional view of the section taken along a line V-V shown in FIG. 3. FIG. 6 is a magnified perspective view of the heat generating element shown in FIG. 3.

In the present embodiment, an example is shown in which the heat generating element 116 according to the above-described first embodiment is used for a heat coagulation cutting forceps for open surgery, the forceps serving as a medical therapeutic instrument, or a treatment apparatus including the heat coagulation cutting forceps for open surgery and a power device according to the second embodiment. Therefore, in the description of the present embodiment, the heat generating element 116 described in the first embodiment is indicated by the same reference numeral, and further explanations of the configuration thereof will not be provided.

As shown in FIG. 3, a key portion of a treatment apparatus 101 is composed of a heat coagulation cutting forceps for open surgery (hereafter simply referred to as forceps) 102 and a power device 103. The forceps 102 is used for subjecting a living-body tissue in a body cavity to various treatments, e.g., coagulation and cutting, by taking advantage of the heat generated based on the electric power supplied. The power device 103 is power supply means for controlling the thermal driving of the forceps 102 by supplying electric power to the forceps 102.

The key portion of the forceps 102 is composed of a first forceps body 105 composed of a rod-shaped member and a second forceps body 107 composed of a rod-shaped member rotatably mounted on the first forceps body 105 through a pivot 106 serving as a pivotal portion.

A first grasping portion (hereafter referred to as jaw) 108 formed into the shape of a free-form surface, for example, a curved shape, in a longitudinal direction (hereafter referred to as principal axis direction) is disposed on the distal-end side of the first forceps body 105. A second jaw 109 formed into the shape having a principal axis in a curved shape is disposed on the distal-end side of the second forceps body 107. The first jaw 108 pairs off with the second jaw 109 and constitutes a treatment portion 110.

A first arm 111 is disposed on the rear side of the first forceps body 105, and a first ring 112 for insertion of a finger is disposed on the proximal-end side of the first arm 111. A cord connection portion 128 is disposed on the proximal end portion of the first ring 112.

A second arm 113 is disposed on the rear side of the second forceps body 107 as in the first forceps body 105, and a second ring 114 for insertion of a finger is disposed on the proximal-end side of the second arm 113.

The first arm 111, the second arm 113, the first ring 112, and the second ring 114 constitute a control portion 115 to perform opening and closing operations of a pair of the first jaw 108 and the second jaw 109 constituting the treatment portion 110.

A heat generating element 116 to apply thermal energy to a living-body tissue is disposed on the first jaw 108 while being located at the position facing the second jaw 109. For details, the heat generating element 116 is mounted on a concave portion 108a formed along the principal axis, on the surface of the first jaw 108 facing the second jaw 109.

Specifically, the heat generating element 116 is mounted along the principal axis, on a concave portion 108a with a heat insulating member 122 (refer to FIG. 5), described below, therebetween in such a manner that the treatment surface 2at, described below, of the substrate 2 is located to face the second jaw 109. The heat generating element 116 may be mounted on the second jaw 109. Furthermore, the heat generating elements may be mounted on both the first jaw 108 and the second jaw 109.

The configuration of the heat generating element 116 is substantially the same as the heat generating element 116 according to the first embodiment described above with reference to FIG. 1 or FIG. 2. However, the principal axis of the heat generating element 116 is formed into the shape in agreement with the curved shape of the principal axis of the first jaw 108. In this manner, the heat generating element 116 can readily be disposed on the first jaw 108 even though the first jaw 108 is in the curved shape.

The position 2at which is a perimeter surface 2a of the substrate 2 in the convex shape pointing downward of the heat generating element 116 and which faces the second jaw 109 serves as a treatment surface in the treatment of, for example, a living-body tissue. The treatment surface 2at is in a blunt shape. In the present embodiment, the treatment surface 2at is constructed into the shape of a partial arc which is a free-form surface and which has a diameter substantially equal to the width of the heat generating element 116. Put another way, the treatment surface 2at is constructed to have a cross section in the shape of a partial arc which is a free-form surface, the cross section being substantially perpendicular to a longitudinal direction of the heat generating element 116.

The perimeter surface 2a (refer to FIG. 2) of the substrate 2 substantially in the convex shape pointing downward of the heat generating element 116 may be provided with a non-adhesive coating made of polytetrafluoroethylene (PTFE) or the like in order to prevent sticking of a living-body tissue in the treatment of the living-body tissue.

As shown in FIG. 6, lead wires 124, 125, 126, and 127 are connected and fixed to respective electrodes 20 disposed on the top surface 116a of the heat generating element 116. The connection and fixing can be performed by welding, brazing, soldering, or the like.

As shown in FIG. 4 and FIG. 5, the upper portion of the heat generating element 116 mounted on the first jaw 108 is covered with a heat insulating member 122 made of a material having a low thermal conductivity and high heat resistance, e.g., polytetrafluoroethylene (PTFE) or a high-performance thermoplastic resin (PEEK (registered trademark)).

The heat insulating member 122 is fit and fixed to the concave portion 108a disposed along the principal axis on the first jaw 108. As shown in FIG. 4, the heat generating element 116 is fixed to the heat insulating member 122 or the first jaw 108 along the principal axis by using pins 121 for fixing a heat generating element.

As shown in FIG. 4 and FIG. 5, a receiving member 123 is disposed on the second jaw 109 while being located at the position facing the heat generating element 116 mounted on the first jaw 108. The receiving member 123 is formed from a resin material, e.g., silicone rubber, fluororubber, or PTFE.

As shown in FIG. 3, the lead wires 124 to 127 connected and fixed to the electrodes 20 of the heat generating element 116 are connected to the cord connection portion 128 disposed at the proximal end portion of the first ring 112 disposed on the proximal-end side of the forceps 102.

Furthermore, one end of a connection cord 129 is connected to a power device 103, and the other end is connected to the cord connection portion 128. A foot switch 104 to perform ON/OFF control of the electric power of the power device 103 is connected to the power device 103 through a foot switch cord 130.

An operation of the thus configured treatment apparatus including the forceps and the power device according to the present embodiment will be described below.

In the treatment of a living-body tissue by using the treatment apparatus 101 of the present embodiment, a surgeon positions the living-body tissue in between the first jaw 108 and the second jaw 109 of the forceps 102.

The surgeon grasps the living-body tissue between the treatment surface 2at of the heat generating element 116 mounted on the first jaw 108 and the receiving member 123 of the second jaw 109 by operating the control portion 115 to close the forceps 102 while the living-body tissue is positioned in between the first jaw 108 and the second jaw 109 of the forceps 102.

After grasping the living-body tissue, the surgeon operates the foot switch 104 so that electric power is supplied from the power device 103 through the connection cord 129, the cord connection portion 128, and the lead wires 124 to 127 to the heat generating element 116, the heat generating portion 4 of the heat generating element 116 is made to generate heat, and the living-body tissue is subjected to a treatment, e.g., coagulation or cutting.

At this time, since the heat generating portion 4 and the treatment surface 2at have been integrated in the heat generating element 116, the efficiency of heat transfer from the heat generating portion 4 to the treatment surface 2at can be significantly increased. Since the heat generating portion 4 is disposed on the top surface of the treatment surface 2at, put another way, on the surface opposite to the treatment surface 2at, as shown in FIG. 6, the heat generating portion 4 can readily be formed even when the heat generating element 116 is in a curved shape along the principal axis.

The electric power is supplied from the power device 103 to the heat generating element 116 by any one of a constant voltage system, a constant current system, and a constant power system, and may be controlled in such a way that the power supply is interrupted or the power supply system is switched when the temperature, time, cumulative amount of power, or the like reaches a threshold value.

Alternatively, the power supply from the power device 103 to the heat generating element 116 may be controlled in such a way that the temperature of the heat generating element 116 is always kept constant or is changed stepwise. This control may be combined with the above-described control in which the power supply is interrupted or the power supply system is switched when a threshold value is reached.

As described above, in the treatment apparatus including the forceps 102 and the power device 103 according to the present embodiment, the heat generating element 116 according to the first embodiment is disposed on the first jaw 108, while the heat generating element 116 has high heat-generation resistance and the uniformity of the temperature distribution in the heat generation is improved, and the living-body tissue is grasped between the treatment surface 2at of the substrate 2 of the heat generating element 116 and the receiving member 123 of the second jaw 109. In addition, the heat generating portion 4 and the treatment surface 2*at* of the substrate 2 is integrated in the heat generating element 116.

In this manner, since the efficiency of heat transfer from the heat generating portion 4 to the treatment surface 2*at* is increased, it is possible to provide the forceps 102 or the treatment apparatus 101 capable of exerting a highly efficient and reliable heat effect on the living body with a uniform temperature distribution and performing stable coagulation or cutting of the living-body tissue.

Even when the principal axis of the heat generating element 116 is formed into the curved shape, since the first jaw 108 of the forceps 102 can be formed into the curved shape, which is an arbitrary free-form surface, along the principal axis, the operability in treatments, e.g., dissecting of the living-body tissue, can be improved.

Modified embodiments will be described below. In the present embodiment described above, the treatment surface 2*at* of the substrate 2 of the heat generating element 116 is in a blunt shape, and is constructed into the shape of a partial arc which is a free-form surface and which has a diameter substantially equal to the width of the heat generating element 116.

However, the shape of the treatment surface 2*at* is not limited to this, and may be changed in accordance with purposes of treatments. In general, as the shape of the treatment surface 2*at* becomes sharper, treatments, e.g., cutting, are readily performed, and as the shape becomes blunter, treatments, e.g., coagulation, are readily performed.

Figure 7:
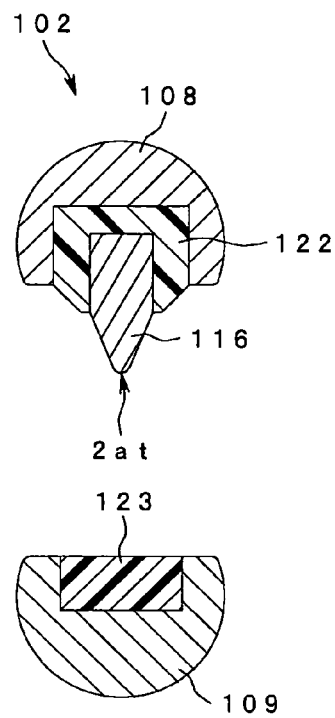
FIG. 7 is a sectional view of a modified example of a treatment surface of the heat generating element shown in FIG. 5.

Specifically, as for a sharper shape, the treatment surface 2*at* may be formed into a shape in which both sides are constructed by inclined surfaces and the distal end portion has a small radius of curvature, as shown in FIG. 7.

Figure 8:
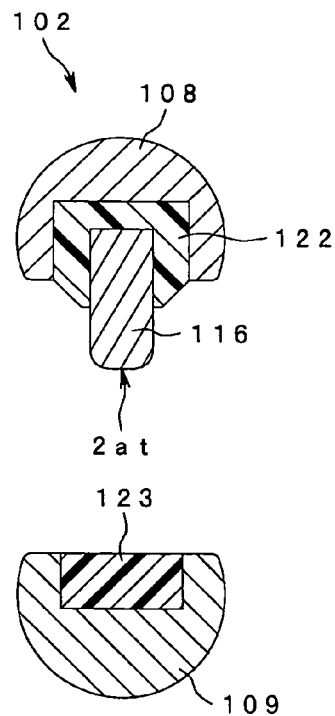
FIG. 8 is a sectional view of another modified example of the treatment surface of the heat generating element shown in FIG. 5.
Figure 9:
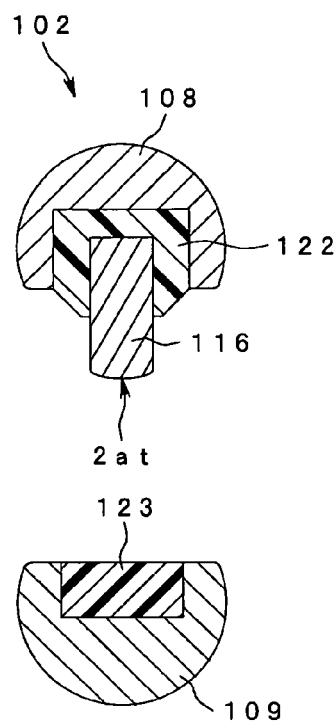
FIG. 9 is a sectional view of another modified example of the treatment surface of the heat generating element shown in FIG. 5.
Figure 10:
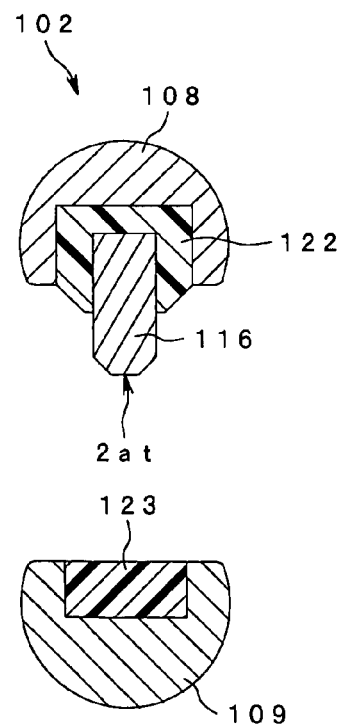
FIG. 10 is a sectional view of another modified example of the treatment surface of the heat generating element shown in FIG. 5.

As for a blunter shape, the treatment surface 2*at* may be formed into a shape in which both edges are chamfered to have a small radius of curvature and the central portion has a flat portion, as shown in FIG. 8. The treatment surface 2*at* may be formed into the shape of a partial arc having a diameter larger than the width of the heat generating element 116, as shown in FIG. 9. Furthermore, the treatment surface 2*at* may be formed into a shape in which both sides of the heat generating element are constructed by inclined surfaces and the distal end portion is made flat, as shown in FIG. 10.

Third Embodiment

Figure 11:
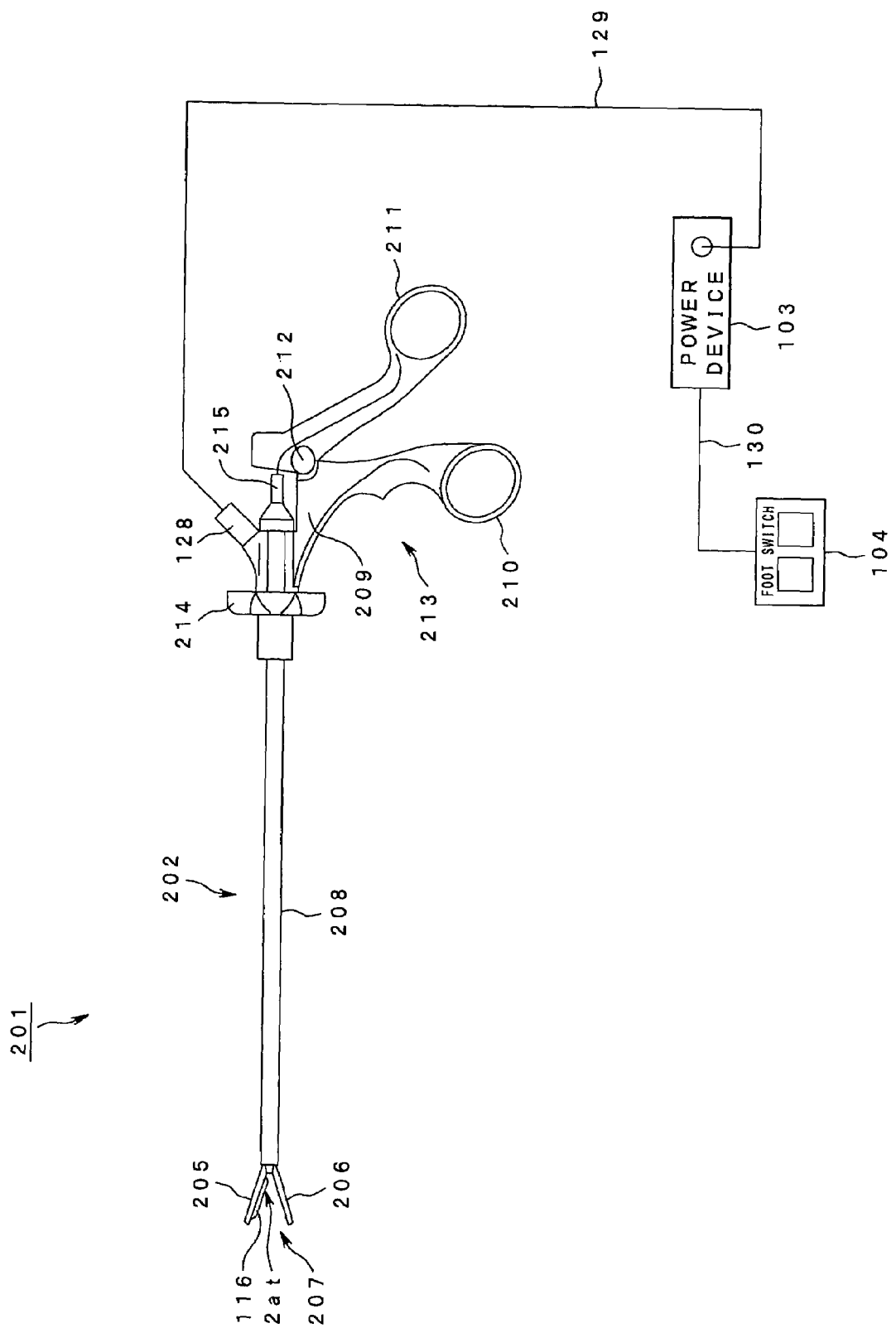
FIG. 11 is a front view showing a configuration of a treatment apparatus including a heat coagulation cutting forceps for laparoscopic surgery, the forceps serving as a medical therapeutic instrument, and a power device according to a third embodiment of the present invention.
Figure 12:
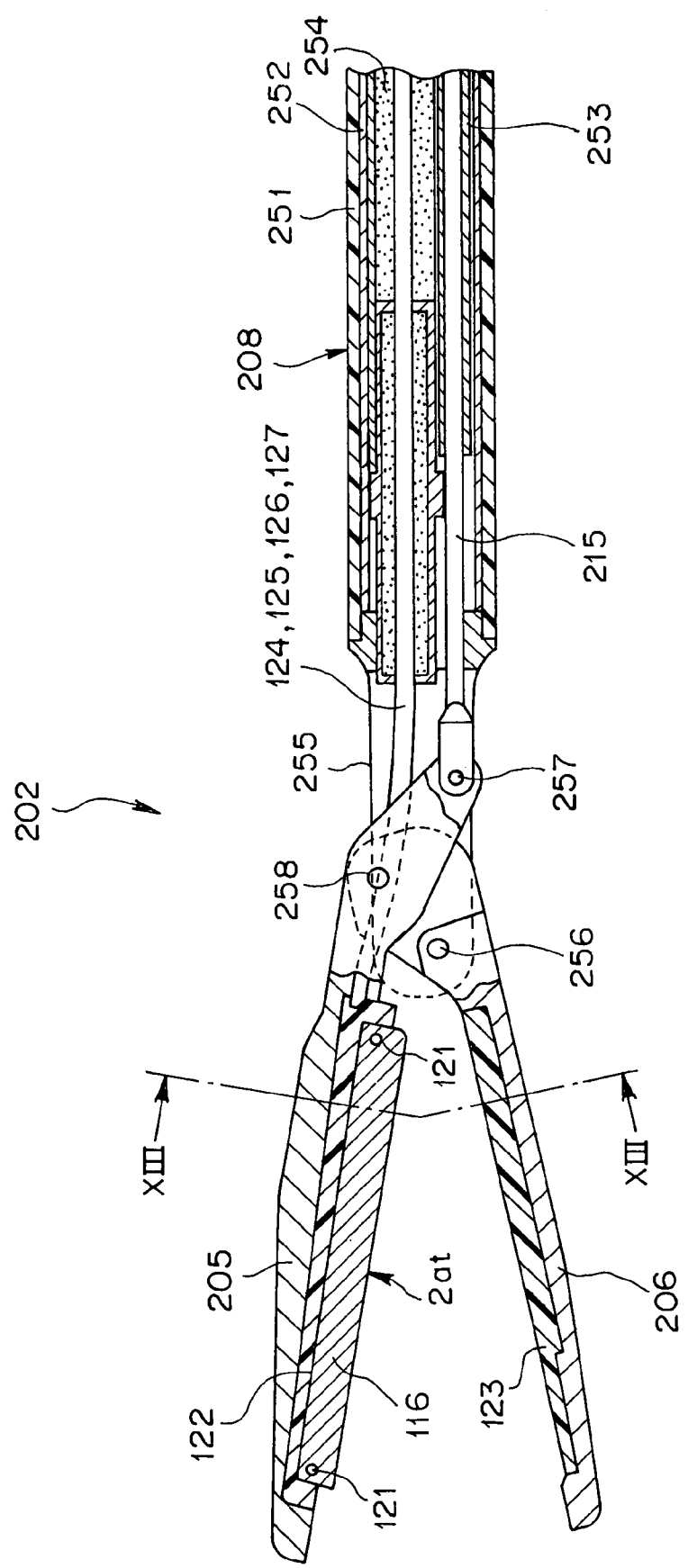
FIG. 12 is a sectional view of a distal end portion of the heat coagulation cutting forceps for laparoscopic surgery shown in FIG. 11.

FIG. 11 is a front view showing a configuration of a treatment apparatus including a heat coagulation cutting forceps for laparoscopic surgery, the forceps serving as a medical therapeutic instrument, and a power device according to a third embodiment of the present invention. FIG. 12 is a sectional view of a distal end portion of the heat coagulation cutting forceps for laparoscopic surgery shown in FIG. 11. FIG. 13 is a sectional view of the section taken along a line XIII-XIII shown in FIG. 12.

In the present embodiment, an example is shown in which the heat generating element 116 according to the above-described first embodiment is used for a heat coagulation cutting forceps for laparoscopic surgery, the forceps serving as a medical therapeutic instrument, or a treatment apparatus including the heat coagulation cutting forceps for laparoscopic surgery and a power device. Therefore, in the description of the present embodiment, the heat generating element 116 described in the first embodiment is indicated by the same reference numeral, and further explanations of the configuration thereof will not be provided.

The configuration of the heat coagulation cutting forceps for laparoscopic surgery or the treatment apparatus including the heat coagulation cutting forceps for laparoscopic surgery and the power device of the present embodiment is different from the configuration of the heat coagulation cutting forceps for open surgery 102 or the treatment apparatus 101 including the heat coagulation cutting forceps for open surgery 102 and the power device 103 shown in FIG. 3 to FIG. 10 in that the heat generating element 116 is disposed on the heat coagulation cutting forceps for laparoscopic surgery. Therefore, only this dissimilarity will be described. The configurations similar to those in the second embodiment are indicated by the same reference numerals, and further explanations thereof will not be provided.

As shown in FIG. 11, a treatment apparatus 201 according to the present embodiment has a configuration including a heat coagulation cutting forceps for laparoscopic surgery (hereafter simply referred to as forceps) 202 used for subjecting a living-body tissue in a body cavity to various treatments, e.g., coagulation and cutting, by taking advantage of the heat generated based on the electric power supplied from the power device 103 serving as power supply means.

The forceps 202 is provided with a slender insertion portion 208, a treatment portion 207 disposed on the distal-end side of the insertion portion 208, and a control portion 213 disposed on the proximal-end side of the insertion portion 208.

The treatment portion 207 is composed of a pair of grasp portions which can be optionally opened and closed, for example, a first jaw 205 formed to have a principal axis in a curved shape, which is a free-form surface, and a second jaw 206 formed into the shape having a principal axis in a curved shape. As in the above-described second embodiment, the first jaw 205 is formed into the shape in agreement with the shape of the principal axis of the heat generating element 116.

A key portion of the control portion 213 is composed of a control portion main body 209, a first handle (hereafter referred to as fixed handle) 210 disposed integrally with the control portion main body 209, a second handle (hereafter referred to as movable handle) 211 rotatably attached to the fixed handle 210 through a pivot 212.

As the control portion 213 is opened and closed by operation, the first jaw 205 and the second jaw 206 of the treatment portion 207 are opened and closed. The control portion main body 209 is provided with a rotation control portion 214 to rotate the insertion portion 208 about the center of axis of the insertion portion 208 in circumferential directions of the axis.

As shown in FIG. 12, an outer tube 251 formed from a pipe having a small diameter is disposed in the insertion portion 208. A channel pipe 252 and a driving shaft channel 253 are parallel disposed along the principal axis in the inside of the outer tube 251.

An insertion space 254 is disposed in the inside of the channel pipe 252, and lead wires 124 to 127 to be connected to the heat generating element 116 are inserted through the channel pipe 252. Furthermore, a driving shaft 215 is inserted through the driving shaft channel 253 in such a manner that the driving shaft 215 can be moved optionally in the principal axis direction. As shown in FIG. 11, the proximal end portion of the driving shaft 215 is coupled to a movable handle 211. The driving shaft 215 is driven to move in the principal axis direction while being operatively associated with the opening and closing operation of the movable handle 211.

As shown in FIG. 12, a bifurcated support member 255 protruding toward the front is disposed at the distal end portion of the insertion portion 208. The proximal-end side of the support member 255 in the principal axis direction is fixed to the front end of the outer tube 251. A pivot pin 256 serving as a pivotal portion is disposed at the bifurcated distal end portion of the support member 255 while penetrating the support member 255 in the direction of penetration.

The proximal end portion of the second jaw 206 in the principal axis direction is rotatably fixed to the support member 255 through the pivot pin 256. The proximal end portion of the first jaw 205 in the principal axis direction is coupled to the driving shaft 215 through a coupling pin 257. Furthermore, the proximal end portion of the second jaw 206 is rotatably fixed to the proximal end portion of the first jaw 205 through a connection pin 258.

Consequently, when the opening and closing operation of the movable handle 211 is performed relative to the fixed handle 210, the driving shaft 215 is driven to move to and fro. As a result, the first jaw 205 having the proximal end portion coupled to the driving shaft 215 is opened and closed relative to the second jaw 206.

The configurations of the first jaw 205 and the second jaw 206 are similar to the configuration in the above-described second embodiment. As shown in FIG. 12 and FIG. 13, the first jaw 205 is provided with a heat generating element 116, a heat insulating member 122, and the like, and the second jaw 206 is provided with a receiving member 123 and the like.

Other configurations and the operations of the forceps 202 and the treatment apparatus 201 including the forceps 202 and the power device 103 are the same as those in the above-described second embodiment. Therefore, further explanations thereof will not be provided.

As described above, in the treatment apparatus 201 including the forceps 202 and the power device 103 according to the present embodiment, the heat generating element 116 according to the first embodiment is disposed on the first jaw 205, while the heat generating element 116 has high heat-generation resistance and the uniformity of the temperature distribution in the heat generation is improved, and as shown in FIG. 12 and FIG. 13, the living-body tissue is grasped between the treatment surface 2*at* of the substrate 2 of the heat generating element 116 and the receiving member 123 of the second jaw 206. In addition, the heat generating portion 4 and the treatment surface 2*at* of the substrate 2 is integrated in the heat generating element 116.

In this manner, since the efficiency of heat transfer from the heat generating portion 4 to the treatment surface 2*at* is increased, it is possible to provide the forceps 202 or the treatment apparatus 201 capable of exerting a highly efficient and reliable heat effect on the living body with a uniform temperature distribution and performing stable coagulation or cutting of the living-body tissue.

Since the principal axis of the heat generating element 116 can be formed into the curved shape, the first jaw 205 of the forceps 202 can also be formed into the curved shape along the principal axis. Therefore, the operability in the treatment, e.g., dissecting of the living-body tissue, can be improved.

Modified embodiments will be described below. In the present embodiment described above, the treatment surface 2*at* of the substrate 2 of the heat generating element 116 is in a blunt shape, and is constructed into the shape of a partial arc which is an arbitrary free-form surface and which has a diameter substantially equal to the width of the heat generating element 116, as shown in FIG. 13, similarly to that in the above-described second embodiment.

However, the shape of the treatment surface 2*at* is not limited to this, and may be changed in accordance with purposes of treatments. The shape may be similar to those shown in FIG. 7 to FIG. 10 in the above-described second embodiment.

Fourth Embodiment

Figure 14:
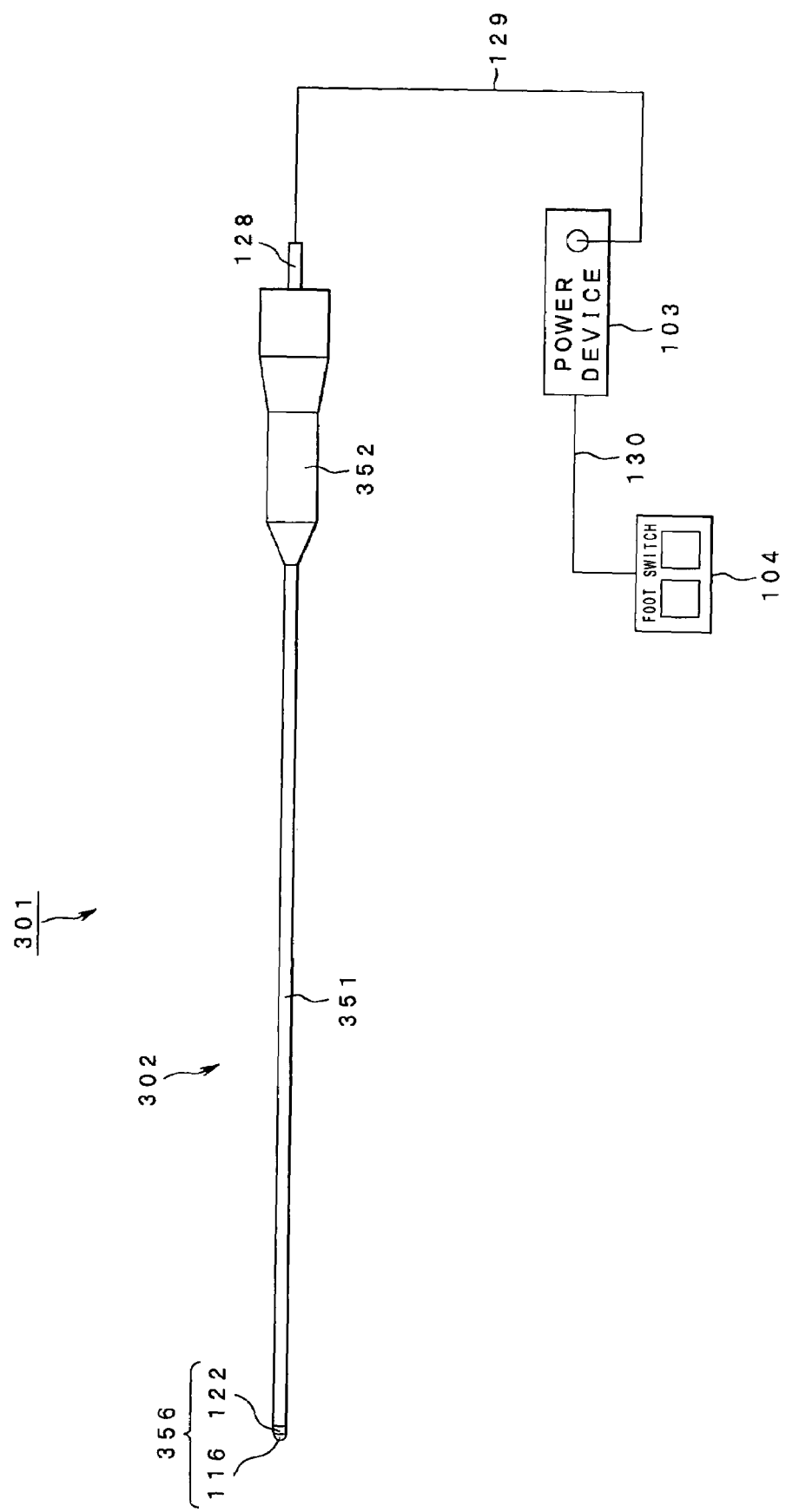
FIG. 14 is a front view showing a configuration of a treatment apparatus including a heat coagulation probe serving as a medical therapeutic instrument and a power device according to a fourth embodiment of the present invention.
Figure 15:
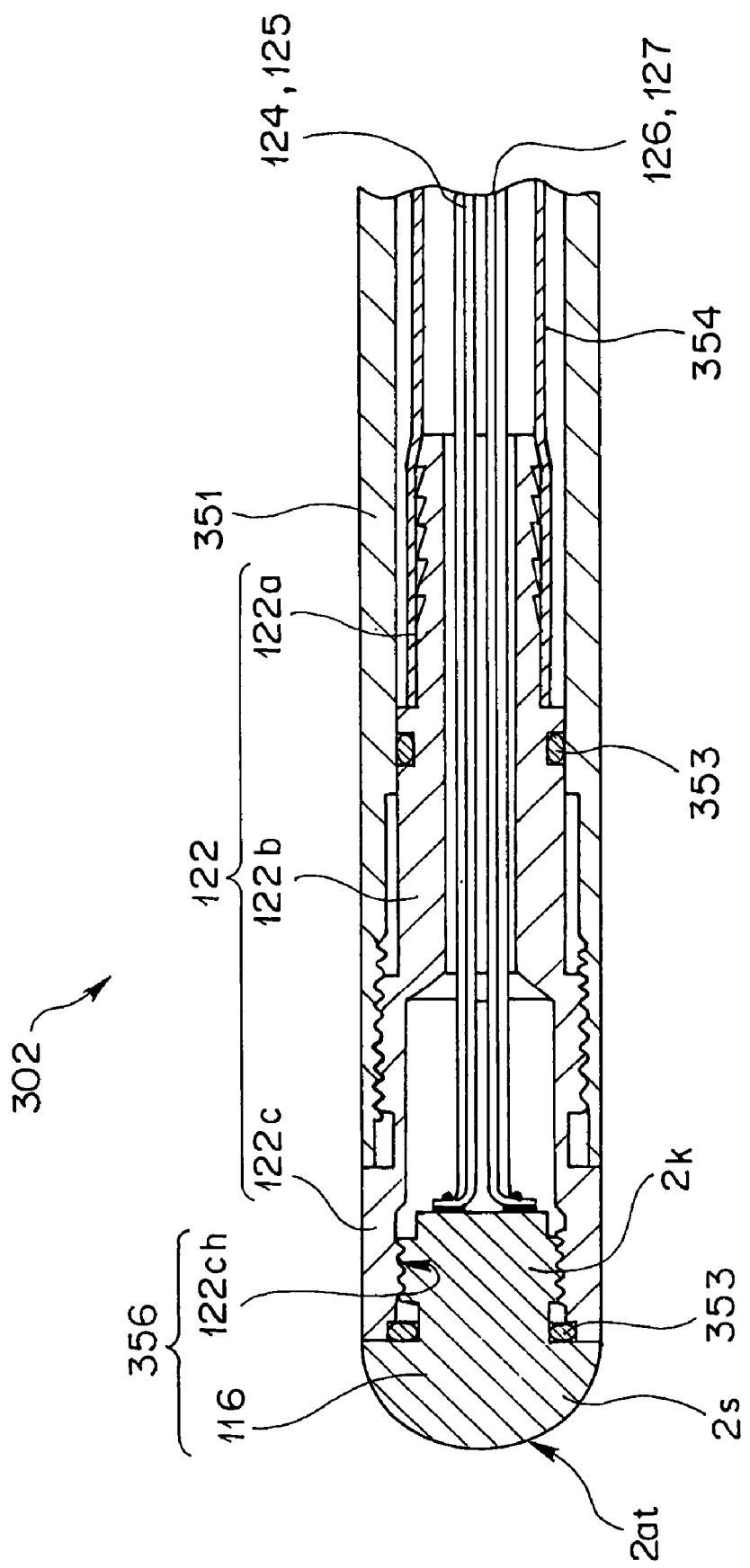
FIG. 15 is a sectional view of a distal end portion of the heat coagulation probe shown in FIG. 14.
Figure 16:
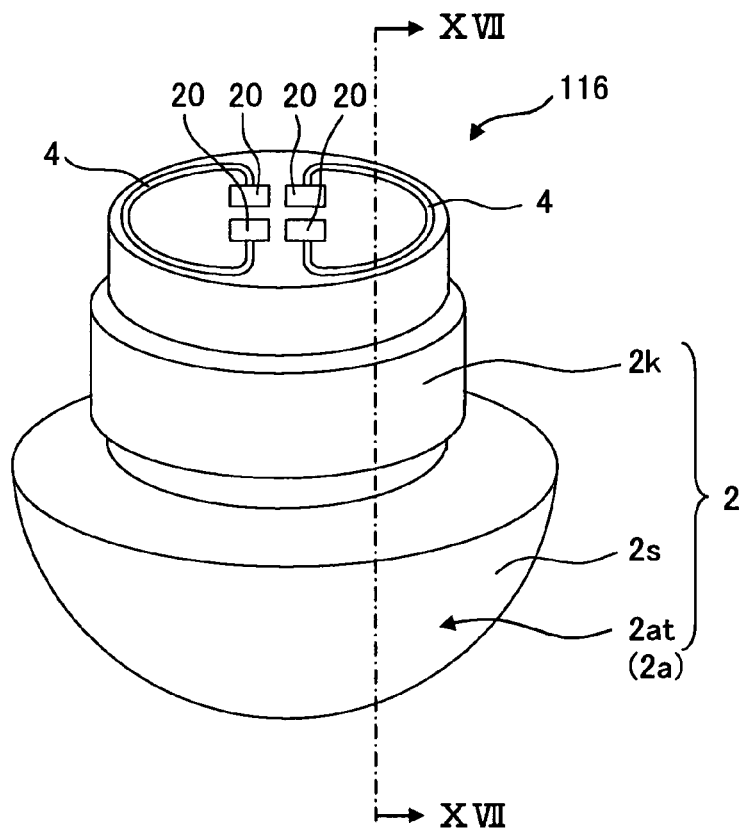
FIG. 16 is a perspective view of a heat generating element disposed at the distal end of a shaft of the heat coagulation probe shown in FIG. 14.
Figure 17:
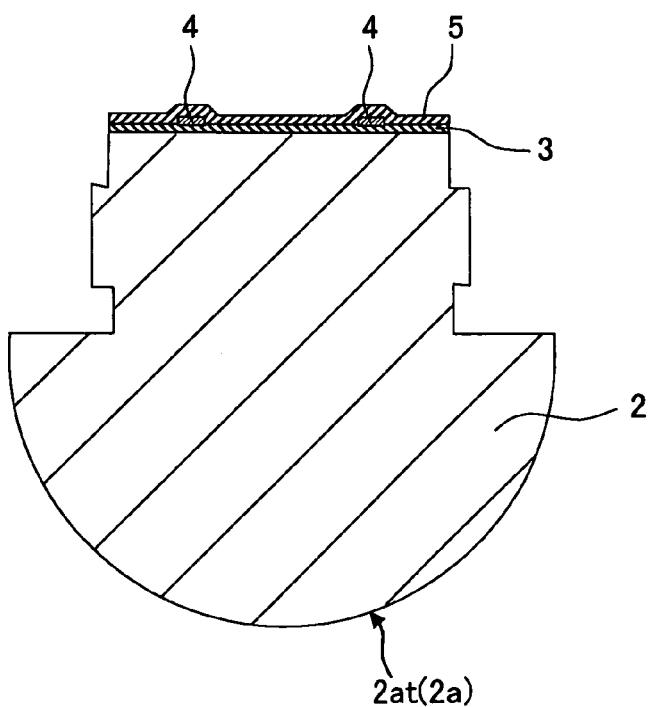
FIG. 17 is a sectional view of the section taken along a line XVII-XVII shown in FIG. 16.

FIG. 14 is a front view showing a configuration of a treatment apparatus including a heat coagulation probe serving as a medical therapeutic instrument and a power device according to the fourth embodiment of the present invention. FIG. 15 is a sectional view of a distal end portion of the heat coagulation probe shown in FIG. 14. FIG. 16 is a perspective view of a heat generating element disposed at the distal end of a shaft of the heat coagulation probe shown in FIG. 14. FIG. 17 is a sectional view of the section taken along a line XVII-XVII shown in FIG. 16.

In the present embodiment, an example is shown in which the heat generating element 116 according to the above-described first embodiment is used for a heat coagulation probe serving as a medical therapeutic instrument or a treatment apparatus including the heat coagulation probe and a power device according to the fourth embodiment. Therefore, in the description of the fourth embodiment, the heat generating element 116 described in the first embodiment is indicated by the same reference numeral, and further explanations of the configuration thereof will not be provided.

The configuration of the heat coagulation probe or the treatment apparatus including the heat coagulation probe and the power device of the present embodiment is different from the configuration of the heat coagulation cutting forceps for open surgery 102 and the treatment apparatus 101 shown in the above-described FIG. 3 to FIG. 10 and the configuration of the heat coagulation cutting forceps for laparoscopic surgery 202 and the treatment apparatus 201 shown in the above-described FIG. 11 to FIG. 13 in that the heat generating element 116 is deformed in agreement with the shape of the distal end of the heat coagulation probe, and is disposed at the distal end of the heat coagulation probe. Therefore, only this dissimilarity will be described. The configurations similar to those in the second embodiment and the third embodiment are indicated by the same reference numerals, and further explanations thereof will not be provided.

As shown in FIG. 14, a treatment apparatus 301 according to the present embodiment has a configuration including a heat coagulation probe (hereafter simply referred to as probe) 302 used for subjecting a living-body tissue to various treatments, e.g., coagulation, by taking advantage of the heat generated based on the electric power supplied from the power device 103 serving as power supply means.

As shown in FIG. 14 and FIG. 15, the probe 302 is provided with a slender shaft 351, a treatment portion 356 disposed on the distal-end side of the shaft 351, and a grip 352 disposed on the proximal-end side of the shaft 351.

The proximal end portion of the shaft 351 is mounted on the distal end of the grip 352 by screw coupling, for example. A cord connection portion 128 is disposed on the proximal end portion of the grip 352. As shown in FIG. 15, a protective tube 354 is disposed in the inside of the shaft 351, and the above-described lead wires 124 to 127 are inserted through the inside of the protective tube 354.

The treatment portion 356 is disposed on the distal end portion of the shaft 351. For details, the treatment portion 356 is composed of the above-described heat insulating member 122 and the heat generating element 116. In the present embodiment, the heat insulating member 122 is formed into a substantially convex shape with steps, and a first projection 122*a* is fit into the inner perimeter on the distal-end side of the protective tube 354.

A second projection 122*b* of the heat insulating member 122 is fit into the inside of the shaft 351 with a watertight O-ring 353 therebetween and is fixed by screw coupling, for example. Furthermore, the lead wires 124 to 127 are also inserted through the inside of the heat insulating member 122.

A hole portion 122ch is bored in the surface on the distal-end side of a base portion 122c of the heat insulating member 122, and the heat generating element 116 is fit into the hole portion 122ch with a watertight O-ring 353 therebetween and is fixed by screw coupling, for example.

In the present embodiment, as shown in FIG. 16 and FIG. 17, the heat generating element 116 is composed of a cylindrical fitting portion 2k in the shape of an outward flange having a small diameter and a hemispherical portion 2s which is connected to the end portion of the fitting portion 2k and which has an outer surface 2a in the shape of a free-form surface constituting a treatment surface 2at. The treatment surface 2at may be constructed into the shape of other than a hemisphere.

In the present embodiment as well, the treatment surface 2at of the hemispherical portion 2s may be provided with a non-adhesive coating made of polytetrafluoroethylene (PTFE) or the like in order to prevent sticking of a living-body tissue in pealing of the living-body tissue.

The fitting portion 2k of the thus configured heat generating element 116 is fit into the hole portion 122ch of the heat insulating member 122 and is fixed by screw coupling, for example. At this time, the ends of the lead wires 124 to 127 are connected to the electrodes 20 of the heat generating element 116, as described above.

Other configurations of the heat generating element 116 and the treatment apparatus 301 are the same as those in the above-described first to third embodiments. Therefore, further explanations thereof will not be provided.

An operation of the thus configured treatment apparatus including the probe and the power device according to the present embodiment will be described below.

In the treatment of a living-body tissue by using the treatment apparatus 301 of the present embodiment, a surgeon brings the treatment surface 2at of the heat generating element 116 fixed to the distal end of the probe 302 into contact with the living-body tissue.

The surgeon operates the foot switch 104 so that electric power is supplied from the power device 103 serving as power supply means through the connection cord 129, the cord connection portion 128, and the lead wires 124 to 127 to the heat generating element 116, the heat generating portion 4 of the heat generating element 116 is made to generate heat, and the living-body tissue is subjected to a treatment, e.g., coagulation. At this time, since the heat generating portion 4 and the treatment surface 2at have been integrated in the heat generating element 116, the efficiency of heat transfer from the heat generating portion 4 to the treatment surface 2at can be significantly increased.

As described above, in the treatment apparatus 301 including the probe 302 and the power device 103 according to the present embodiment, the heat generating element 116 according to the first embodiment is disposed on the distal end of the shaft 351, while the heat generating element 116 has high heat-generation resistance and the uniformity of the temperature distribution in the heat generation is improved, and the treatment surface 2at of the substrate 2 of the heat generating element 116 is brought into contact with the living-body tissue. In addition, the heat generating portion 4 and the treatment surface 2at of the substrate 2 are integrated in the heat generating element 116.

In this manner, since the efficiency of heat transfer from the heat generating portion 4 to the treatment surface 2at is increased, it is possible to provide the probe 302 or the treatment apparatus 301 capable of exerting a highly efficient and reliable heat effect on the living body with a uniform temperature distribution and performing stable coagulation of the living-body tissue.

Modified embodiments will be described below. In the present embodiment described above, the medical therapeutic instrument is exemplified by the probe. However, the medical therapeutic instrument is not limited to this, and as a matter of course, any medical therapeutic instrument may be applied as long as a living-body tissue is treated by an application of heat.

In the present embodiment described above, the heat generating element 116 is composed of the cylindrical fitting portion 2k in the shape of an outward flange having a small diameter and the hemispherical portion 2s which is connected to the end portion of the fitting portion 2k and which has the outer surface 2a in the shape of a free-form surface constituting the treatment surface 2at. However, the structure is not limited to this, and any structure may be adopted as long as the heat generating element can be fixed to the distal end of the shaft 351. The treatment surface 2at may formed into an optimum shape selected in accordance with the purpose of the treatment, as a matter of course.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A heat generating element comprising at least:
a substrate;
an insulating film disposed on the substrate;
a heat generating portion provided with a thin film resistor disposed on at least a part of the insulating film; and
a protective film disposed on the insulating film and the heat generating portion,
wherein the substrate and the heat generating portion are formed of molybdenum.

2. A medical therapeutic instrument implementing a heat generating element, the medical therapeutic instrument comprising:
a heat generating element including at least a substrate, an insulating film disposed on the substrate, a heat generating portion provided with a thin film resistor disposed on at least a part of the insulating film, and a protective film disposed on the insulating film and the heat generating portions, the substrate and the heat generating portion being formed of molybdenum; and
a treatment portion including the heat generating element to heat a living body tissue by using the heat generated from the heat generating element and treat the living-body tissue,
wherein the heat generating element is mounted on the treatment portion in such a manner that an outer surface of the substrate of the heat generating element serves as a treatment surface in the treatment of the living-body tissue.

3. The medical therapeutic instrument implementing a heat generating element according to claim 2, wherein the treatment portion comprises a pair of jaws which are opened and closed through a pivotal portion disposed at the proximal end portions, and the heat generation element is mounted on at least one jaw of the pair of jaws.

4. The medical therapeutic instrument implementing a heat generating element according to claim 2, wherein the treatment surface of the heat generating element is in the shape of a free-form surface.

5. The medical therapeutic instrument implementing a heat generating element according to claim 3, wherein the treatment surface of the heat generating element is in the shape of a free-form surface.

6. The medical therapeutic instrument implementing a heat generating element according to claim 3, wherein the treatment surface of the heat generating element mounted on the at least one of the jaws is in the shape of a free-form surface in a longitudinal direction while the shape is in accordance with the shape of the at least one of the jaws provided with the heat generating element in the longitudinal direction.

7. The medical therapeutic instrument implementing a heat generating element according to claim 3, wherein the treatment surface of the heat generating element mounted on the at least one of the jaws has a cross section in the shape of a free-form surface, the cross section substantially perpendicular to a longitudinal direction.

8. The medical therapeutic instrument implementing a heat generating element according to claim 6, wherein the treatment surface of the heat generating element mounted on the at least one of the jaws has a cross section in the shape of a free-form surface, the cross section substantially perpendicular to a longitudinal direction.

9. The medical therapeutic instrument implementing a heat generating element according to claim 2, wherein the heat generating element comprises a plurality of heat generating portions.

10. The medical therapeutic instrument implementing a heat generating element according to claim 3, wherein the heat generating element comprises a plurality of heat generating portions.

11. The medical therapeutic instrument implementing a heat generating element according to claim 4, wherein the heat generating element comprises a plurality of heat generating portions.

12. The medical therapeutic instrument implementing a heat generating element according to claim 5, wherein the heat generating element comprises a plurality of heat generating portions.

13. The medical therapeutic instrument implementing a heat generating element according to claim 6, wherein the heat generating element comprises a plurality of heat generating portions.

14. The medical therapeutic instrument implementing a heat generating element according to claim 7, wherein the heat generating element comprises a plurality of heat generating portions.

15. The medical therapeutic instrument implementing a heat generating element according to claim 8, wherein the heat generating element comprises a plurality of heat generating portions.

16. A treatment apparatus comprising:
a medical therapeutic instrument implementing a heat generating element and a treatment portion, the heat generating element including at least a substrate, an insulating film disposed on the substrate, a heat generating portion provided with a thin film resistor disposed on at least a part of the insulating film, and a protective film disposed on the insulating film and the heat generating portion, the substrate and the heat generating portion being formed of molybdenum, and the treatment portion including the heat generating element to heat a living body tissue by using the heat generated from the heat generating element and treat the living-body tissue wherein the heat generating element is mounted on the treatment portion in such a manner that an outer surface of the substrate of the heat generating element serves as a treatment surface in the treatment of the living-body tissue; and
power supply means to supply electric power to the heat generating element disposed on the medical therapeutic instrument.

17. The treatment apparatus according to claim 16, wherein the treatment portion comprises a pair of jaws which are opened and closed through a pivotal portion disposed at the proximal end portions, and the heat generation element is mounted on at least one jaw of the pair of jaws.

18. The treatment apparatus according to claim 16, wherein the treatment surface of the heat generating element is in the shape of a free-form surface.

19. The treatment apparatus according to claim 17, wherein the treatment surface of the heat generating element is in the shape of a free-form surface.

20. The treatment apparatus according to claim 17, wherein the treatment surface of the heat generating element mounted on the at least one of the jaws is in the shape of a free-form surface in a longitudinal direction while the shape is in accordance with the shape of the at least one of the jaws provided with the heat generating element in the longitudinal direction.

21. The treatment apparatus according to claim 17, wherein the treatment surface of the heat generating element mounted on the at least one of the jaws has a cross section in the shape of a free-form surface, the cross section substantially perpendicular to a longitudinal direction.

22. The treatment apparatus according to claim 20, wherein the treatment surface of the heat generating element mounted on the at least one of the jaws has a cross section in the shape of a free-form surface, the cross section substantially perpendicular to the longitudinal direction.

23. The treatment apparatus according to claim 16, wherein the heat generating element comprises a plurality of heat generating portions.

24. The treatment apparatus according to claim 17, wherein the heat generating element comprises a plurality of heat generating portions.

25. The treatment apparatus according to claim 18, wherein the heat generating element comprises a plurality of heat generating portions.

26. The treatment apparatus according to claim 19, wherein the heat generating element comprises a plurality of heat generating portions.

27. The treatment apparatus according to claim 20, wherein the heat generating element comprises a plurality of heat generating portions.

28. The treatment apparatus according to claim 21, wherein the heat generating element comprises a plurality of heat generating portions.

29. The treatment apparatus according to claim 22, wherein the heat generating element comprises a plurality of heat generating portions.

* * * * *